United States Patent [19]

Nusbaum

[11] 4,009,494
[45] Mar. 1, 1977

[54] PROTECTIVE COVERING

[76] Inventor: Max J. Nusbaum, 30 Arlo Road, Staten Island, N.Y. 10301

[22] Filed: Oct. 28, 1975

[21] Appl. No.: 626,312

[52] U.S. Cl. .................................. 2/2; 2/46; 2/48; 128/379; 128/132 R
[51] Int. Cl.² ................................. A41D 13/00
[58] Field of Search ......................... 2/46–52, 2/2, 1; 128/78, 132 R, 132 D, 82, DIG. 15, 379

[56] References Cited

UNITED STATES PATENTS

| 115,238 | 5/1871 | Raiford | 2/2 X |
| 353,575 | 11/1886 | Morrison | 2/52 X |
| 796,695 | 8/1905 | Blake | 2/52 |
| 1,364,746 | 1/1921 | Goodman | 2/52 |
| 1,474,415 | 11/1923 | Glassbrennor | 2/48 |
| 2,655,659 | 10/1953 | Swearingen | 2/52 |
| 3,045,244 | 7/1962 | Schwartz | 2/52 |
| 3,182,656 | 5/1965 | Pyne | 128/132 D |
| 3,332,417 | 7/1967 | Blandford et al. | 128/132 R |

Primary Examiner—G. V. Larkin
Attorney, Agent, or Firm—Richard L. Miller

[57] ABSTRACT

A protective covering which can prevent water from contacting certain portions of the body, such as the abdomen. The covering includes a sheet of flexible fluid impervious material with a fastening device, such as a velcro fastener adjacent its two end portions permitting the sheet to be placed around the body and held by overlapping the end portions. A flexible foam rod is placed along the top of the sheet; the rod being covered with a flexible sleeve. One end of the rod is uncovered and at the opposite end the sleeve is open ended, so that as the sheet wraps around the body portion, the uncovered edge of the rod can telescopically fit into the open end of the sleeve. The covered rod forms a seal against the body for preventing water from reaching the body portion.

9 Claims, 6 Drawing Figures

PROTECTIVE COVERING

BACKGROUND OF THE INVENTION

1. Field of the Invention

This invention relates to protective covering and more particularly to a shower protector for body portions, such as the torso of the body.

2. Description of the Prior Art

It is frequently necessary to protect various portions of the body from water on other contaminants. For example, when a portion of the body has been wounded or is recovering from an operation, doctors will frequently warn patients to avoid contaminants getting into the wound. Additionally, when an area has been bandaged or when a limb has a cast on it, it is necessary to prevent water from getting into the bandage or cast. A further example occurs following abdominal surgery where a colostomy has been performed on the patient. When the patient in such condition needs to take a shower, it is necessary to protect the bandage or colostomy or other part of the body which is affected.

It has generally been known in the prior art to provide such protective coverings which are also worn all the time over the cast or bandage. Such protectors are made out of plastic or other impervious material which is formed as a sack or bag and is placed over the limb bearing the cast, bandage, or the like. In order to maintain the plastic bag over the affected limb, it must be securely fastened to the body portion utilizing tapes, bands, special ties, or various other fasteners. Such fasteners are generally difficult to attach onto the body and require much time and effort to properly secure them. However, since these plastic bags remain on the affected area for long periods of time, frequently weeks or months, the one time effect needed to properly place the protective covering over the limb is tolerated.

Many of the protective coverings of the prior art also include built in supports for the limbs such as knee supports, or splints. These must also be maintained in place by additional ties or tapes which increase the complexity of applying the protective covering onto the body. Most of the prior art coverings completely enclose the limb, so that a proper ambient atmosphere can be contained within the sack around the limb and prevent the sack from contacting and rubbing against the cast, bandage, or the like.

While such known protective coverings do in fact provide water protection to the affected area, they have not been found suitable for quick installation and removal. For example, in certain cases, such as with colostomy patients, it is not necessary to wear the protective covering all the time. Only when taking a shower must the colostomy be protected. The coverings of the prior art would require too much difficulty to tie and tape the plastic sack around the portion of the body in order to prevent water from entering the colostomy. Furthermore, for certain parts of the body, namely the torso, the prior art plastic enclosurers, in the form of sacks or bags cannot be utilized. In addition, the prior art devices require that both the top and bottom of the covering be sealed against the body. While this may be suitable for such portions as a knee, arm, etc., when injuries of the torso require large bandages or when a colostomy has been performed on the stomach area, it is not feasible to have both the top and bottom of the enclosure sealed against the body since the size of the bulge caused by the bandage or colostomy may vary greatly and may not permit standardized devices which will close at both the upper and lower portions thereof.

SUMMARY OF THE INVENTION

It is therefore an object of the present invention to provide a protective covering which is so constructed that it is not subject to the foregoing disadvantages.

It is a further object of the invention to provide a protective covering which is simple and rugged in construction, yet can be fabricated by mass production methods at an appreciably lower cost than prior devices designed to serve similar functions.

It is another object of the present invention to provide a protective covering which can be easily placed around a body portion by a patient and easily removed.

It is yet a further object of the present invention to provide a protective covering which is particularly suitable for preventing water from contacting the portion of the body protected.

Still another object of the present invention is to provide a protective covering which can be placed around the torso of the body and prevent water from contacting portions there under.

Still another object of the present invention is to provide a protective covering which is particularly suitable for abdominal use.

Still a further object of the present invention is to provide a protective covering which can be utilized in conjunction with a colostomy to prevent water from contacting the colostomy area.

Still another object of the present invention is to provide a protective covering which has a top portion which seals against the body for preventing water from getting thereunder, and has a bottom portion which fits around the torso of the body as a skirt.

Yet another object of the present invention is to provide a protective covering which can be manufactured in different sizes to allow for various sized patients.

These and other objects, features and advantages of the invention will in part, be pointed out with particularity, and will, in part, become obvious from the following description of the invention, taken in conjunction with the accompanying drawings, which form an integral part thereof.

Briefly the invention provides a protective covering for preventing water from contacting a portion of the body. The protective covering includes a sheet of flexible fluid-impervious material which has a front and back surface as well as a top, bottom and two side edges. The sheet is sized so that the edges thereof overlap when the sheet is placed around the body portion being protected. Fastening means hold the edges in overlapping relationship to thereby retain the sheet around the body portion. A flexible rod extends along the greater part of the top of the sheet from one edge thereof. An open ended flexible sleeve extends from the other edge of the sheet and covers at least part of the flexible rod. The open end of the sleeve telescopically receives the uncovered part of the rod when the sheet is placed around the body portion. The covered rod forms a seal against the body for preventing water from reaching the body portions.

In an embodiment of the invention, the part of the sleeve which telescopically receives the rod includes a long longitudinal slot to accommodate passage of the edge through the slot. The fastening means can be any of various types such as sections of velcro fasteners, or hook and eye fasteners, or other similar fastening means.

BRIEF DESCRIPTION OF THE DRAWING

In the drawing.

In the various figures of the drawing, like reference characters designate like parts.

DESCRIPTION OF THE PREFERRED EMBODIMENT

Figure 1:
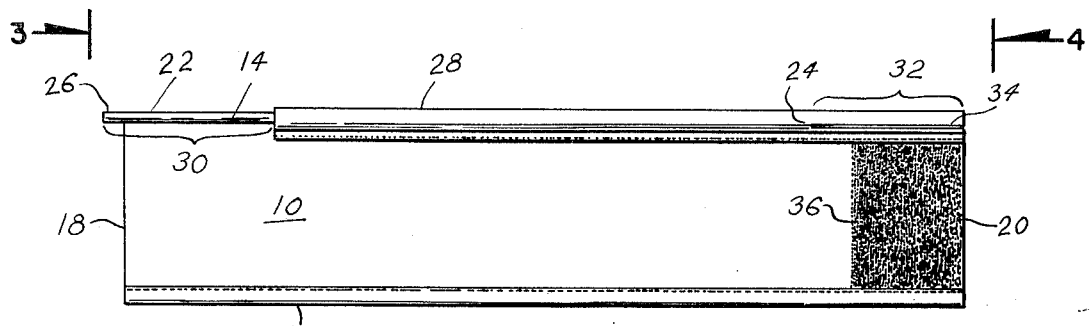
FIG. 1 is a front view of the protective covering in accordance with the present invention.
Figure 2:
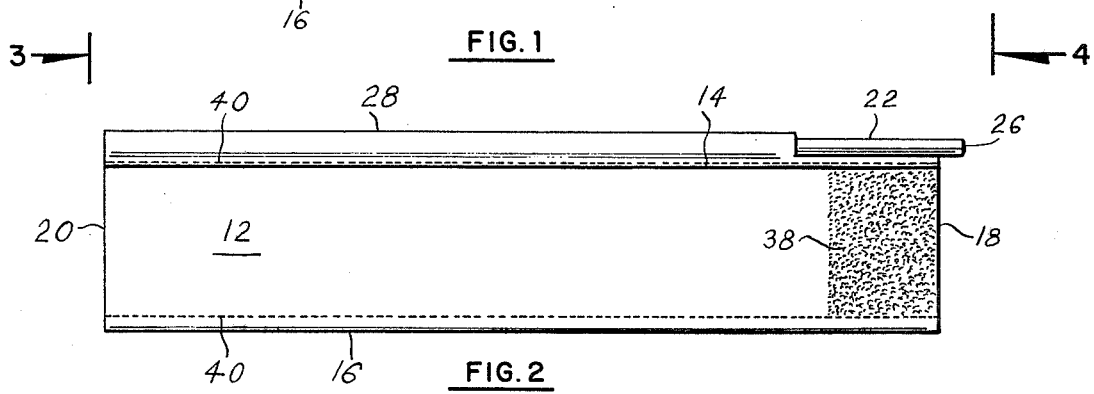
FIG. 2 is a rear view of the protective covering in accordance with the present invention.
Figures 3, 4, 5:
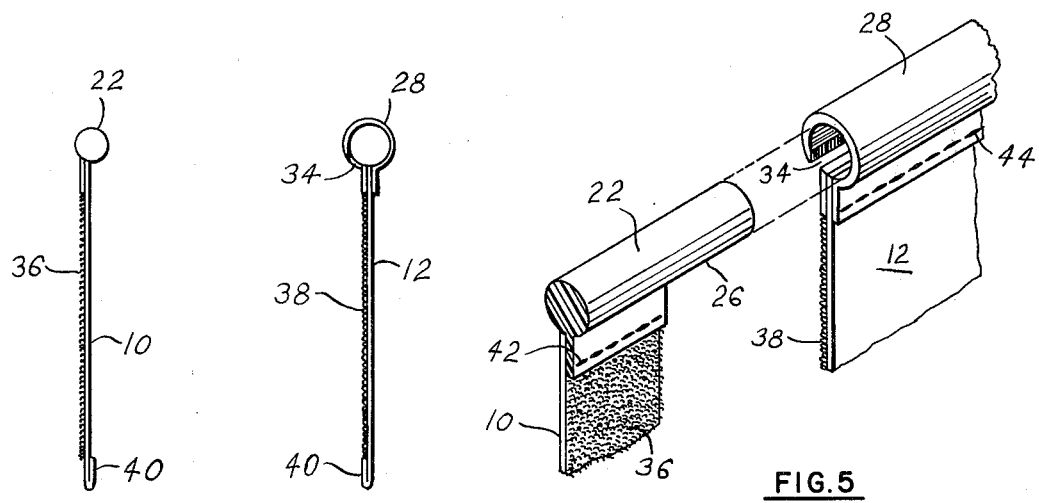
FIG. 3 is a side view taken along 3—3 of FIG. 1.
FIG. 4 is a side view taken along line 4—4 of FIG. 1.
FIG. 5 is a partially broken away perspective view showing the telescopic receiving of the rod in the sleeve when the protective covering is placed around the body.

Referring to FIGS. 1-5, the protective covering includes sheet of flexible fluid-impervious material having a front surface 10 and a rear surface 12. The sheet is shown of approximately rectangular shape and includes a top edge 14, a bottom edge 16, and two side edges 18 and 20. It will be noted the FIG. 2, which represents the rear view is flipped over from that of FIG. 1 such that the right end of FIG. 1 is the same as the left end of FIG. 2.

Attached to the top edge 14 is a flexible rod 22 which is positioned along the greater part of the top, from the edge 18 and until approximately the point 24. It is also noted that the rod extends past the edge at 26. Placed over substantially the greater part of the rod is a sleeve 28 which commences at the opposite edge 20 of the sheet and continues along the greater part of the top. The rod 22 is covered by the sleeve 28.

A portion of the rod 30 remains uncovered and a portion of the sleeve 32 remains open ended without any rod therein. A slot 34 is longitudinally placed at the base of the section 32 which is open ended.

A fastening means is placed on the end portions of the front and rear surface 10, 12 adjacent to the edges 18 and 20. By way of example, the mating sections of a velcro fastener are shown with part of the nap placed adjacent the edge 20 on the front surface 10, and the mating portion placed adjacent the edge 18 on the back portion 12. The bottom edge 16 is shown with a hem 40 which is shown folded toward the front surface 10.

The operation of the device heretofore described is as follows. The size of the device is made long enough to permit the edges 18 and 20 to overlap when the protective covering is placed about a portion of the body. By way of example, assume a patient who has a colostomy and wishes to place the protective covering around his abdomen to protect the abdominal surgery while taking a shower. The patient wraps the protective covering around the abdomen permitting the edges to overlap. The end of the rod 22, specifically the portion 30, telescopically fits into the open ended portion of the sleeves 28, specifically the portion 32. To facilitate entry of the rod into the sleeve, the rod extends slightly past the edge, at the point 26. As the rod 22 slides into the sleeve, the longitudinal slot 34 permits the sheet surface to slide through the slot. The patient continues to telescopically place the uncovered rod into the open-ended sleeve until a tight fit is formed around the abdominal area. The edges which overlap can then be sealed by pressing together the two parts of the velcro material 36, 38. The protective covering is then held in tight fit around the abdomen. The covered rod being flexible conforms to the body configuration and forms a tight seal against the body preventing water from flowing thereunder and thereby protecting the abdominal surgery and the colostomy. It is noted that when in place, the bottom edge of the covering is free to hang over the abdominal portion as a skirt. This permits various sized colostomies or bandages to be covered by the protective covering without causing excessive bulge or difficulty in maintaining the protective covering sealed about the body portion to be protected.

To remove the protective covering, the patient simply opens the fastening device by pulling apart the velcro portions. He can then slide the rod out of the sleeve or unsnap or unhook the fastening device and separate the two portions to remove the covering sheet from his body.

The sheet of flexible fluid-impervious material can be constructed of clear plastic or rubber material, or any form of rubberized material or the like. The flexible rod can be such material as foam, other sponge material, rubber, plastic or other similar resilient materials. Similarly, the sleeve can be constructed of a plasticized or rubberized material or any type of other waterproof material. The rod and the sleeve can be attached to the top portion of the sheet by sewing, electronically sealing, or by other type of fastening. In the embodiment shown, the portions are sewn by means of the stitches 40 which connect the sleeve to the sheet, and by stiches 42 which connect the rod to the sheet. The velcro can also be sewn, glued or electronically sealed onto the end portion of the sheet. By way of example, a typical sheet can be approximately 6 inches wide and of a length to fit around the girth of a body torso with additional length being provided to permit the overlapping relationship of the end portions. The length can also be manufactured in various sizes such as small, medium, large, etc. to permit use by various sized patients. The bottom edge is shown hemmed and can be done by stitching or electronically sealing. The bottom ends could also be left raw. The rod can be approximately ½ inch or ¾ inch in diameter, but can also be varied.

Figure 6:
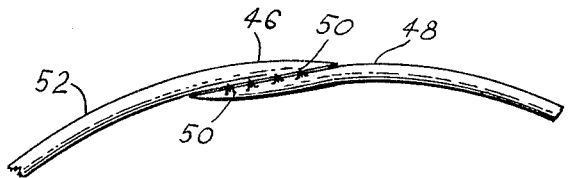
FIG. 6 is a partially broken away top view of the overlapping edges of the protective covering in accordance with another embodiment of the present invention.

Referring now to FIG. 6 there will be shown an alternate embodiment for fastening the overlapping edges together. The overlapping edges 46, 48 are shown interconnected by means of hook and eye assemblies 50. One section of the hook and eye or snap assembly is placed on the front surface of the end 48, while the other section of the assembly is placed on the back surface of the end 46. The patient can then place the sheet around his body portion and hook together the end portions to provide a tight seal. A number of hooks are provided so that he can properly fit the sheet about his body and provide a tight fit, whereby the covered rod 52 will form a seal against his body and a barrier preventing water from penetrating underneath the protective covering.

It will be seen from the foregoing description that the protective covering of the present invention is easily applied and removed, and can be easily utilized as a temporary protective covering while taking a shower.

Furthermore, it provides a water tight seal thereby protecting the colostomy, bandage, or other body portion which need be protected. Also, the bottom of the device remains loose so that it can accommodate various sized bandages, colostomies, or the like, which are to be protected. Additionally, the protective covering can be utilized with body portions such as the torso, where usual sacks and plastic bags could not be utilized as protective coverings.

There has been disclosed heretofore the best embodiments of the invention presently contemplated. However, it is to be understood that various changes and modifications may be made thereto without departing from the spirit of the invention.

What is claimed is:

1. A protective covering for preventing water from contacting a portion of the body, comprising:

a sheet of flexible fluid-impervious material having a front and back surface, and a top, bottom and two side edges, said sheet being sized so that the edges thereof overlap when placed on the body portion, fastening means for holding said edges in overlapping relationship to retain said sheet around the body portion;

a flexible rod attached to and extending along the greater part of the top of the sheet from one edge thereof, and an open ended flexible sleeve attached to the top of the sheet and extending from the other edge thereof, said sleeve covering at least a part of said flexible rod, the open end of said sleeve telescopically receiving the uncovered part of the rod when said sheet encircles said body portion, wherein the covered rod forms a seal against the body for preventing water from reaching the body portion, and wherein the part of said sleeve which telescopically receives said rod includes a longitudinal slot therein to accommodate passage of said one edge therethrough.

2. A protective covering as in claim 1 and wherein said fastening means comprises mating sections of velcro fastener means, one section of which is positioned on the front surface adjacent one edge of the sheet and the other section positioned on the back surface adjacent the other edge of the sheet.

3. A protective covering as in claim 1 and wherein said fastening means includes hook and eye fastener means, one part of which is connected to the front surface adjacent one edge of the sheet and the other part of which is connected to the back surface adjacent the other edge of the sheet.

4. A protective covering as in claim 1 wherein the bottom of the sheet is hemmed.

5. A protective covering as in claim 1 and wherein the lower part of the sheet can hang loosely about the body portion as a skirt.

6. A protective covering as in claim 1 and wherein at least one of said rod, sheet and sleeve is of rubberized material.

7. A protective covering as in claim 1 and wherein at least one of said rod, sheet, and sleeve is of plastic material.

8. A protective covering as in claim 1 and wherein the uncovered portion of said flexible rod extends slightly past said one edge.

9. A protective covering as in claim 1 and wherein said rod and sleeve are electrically heat sealed to said sheet.

* * * * *